United States Patent [19]
Chun

[11] Patent Number: 5,726,454
[45] Date of Patent: Mar. 10, 1998

[54] TRIPOD FOR POLISHING A SAMPLE AND FOR VIEWING THE SAMPLE UNDER A MICROSCOPE

[75] Inventor: Li Meng Chun, Taipei, Taiwan

[73] Assignee: Taiwan Semiconductor Manufacturing Company, Ltd., Hsinchu, Taiwan

[21] Appl. No.: 642,362

[22] Filed: May 3, 1996

[51] Int. Cl.⁶ .................................................. H01J 37/20
[52] U.S. Cl. .............................. 250/442.11; 250/306
[58] Field of Search ........................ 250/306, 442.11, 250/440.11, 307

[56] References Cited

U.S. PATENT DOCUMENTS

| | | | |
|---|---|---|---|
| 4,785,177 | 11/1988 | Besocke | 250/442.11 |
| 4,788,797 | 12/1988 | Kane et al. | 51/170 PT |
| 4,894,537 | 1/1990 | Blackford et al. | 250/306 |
| 4,895,033 | 1/1990 | Voss et al. | 73/364.91 |
| 5,033,834 | 7/1991 | Corder et al. | 350/529 |
| 5,041,783 | 8/1991 | Ohta et al. | 250/306 |
| 5,256,876 | 10/1993 | Hazaki et al. | 250/306 |
| 5,416,414 | 5/1995 | Mansfield et al. | 324/318 |
| 5,479,013 | 12/1995 | Forster et al. | 250/442.11 |
| 5,508,517 | 4/1996 | Onuki et al. | 250/306 |

*Primary Examiner*—Bruce Anderson
*Attorney, Agent, or Firm*—Goerge O. Saile; William J. Stoffel

[57] ABSTRACT

A sample holder tripod for grinding a square edge on a sample and for observing the sample with a microscope is provided. The sample tripod comprises: a tripod base, a support, two adjustable micrometer leg assemblies, a sample stage and a grinding bubble indicator. The micrometer leg assembles are mounted to the tripod through a micrometer mounting holes. The stage has a means to mount a sample. The sample holder tripod can be positioned to view the sample in a top down view and cross-sectional view without having to re-focus the microscope.

18 Claims, 6 Drawing Sheets

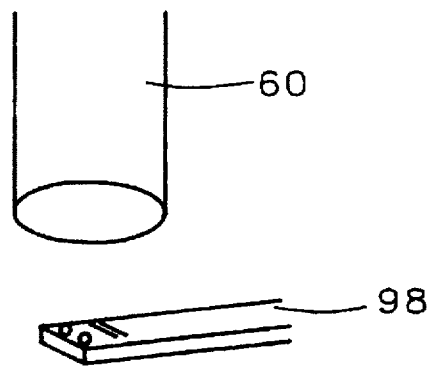
FIG. 1A - Prior Art
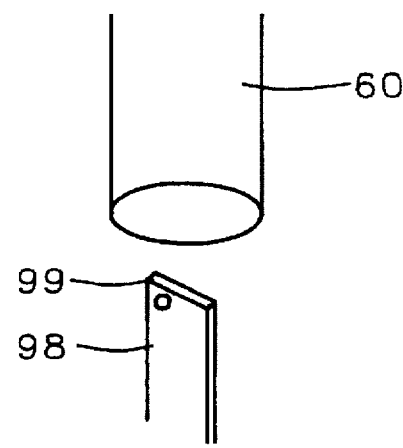
FIG. 1B - Prior Art
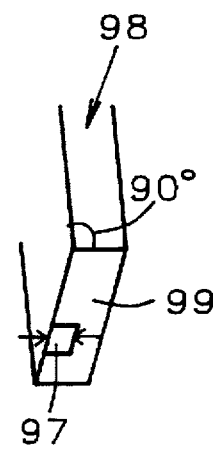
FIG. 1C - Prior Art

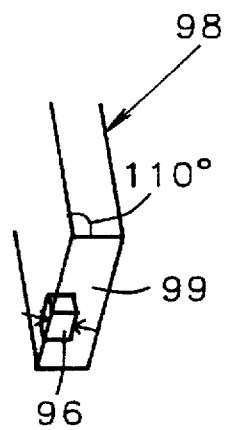
FIG. 1D - Prior Art
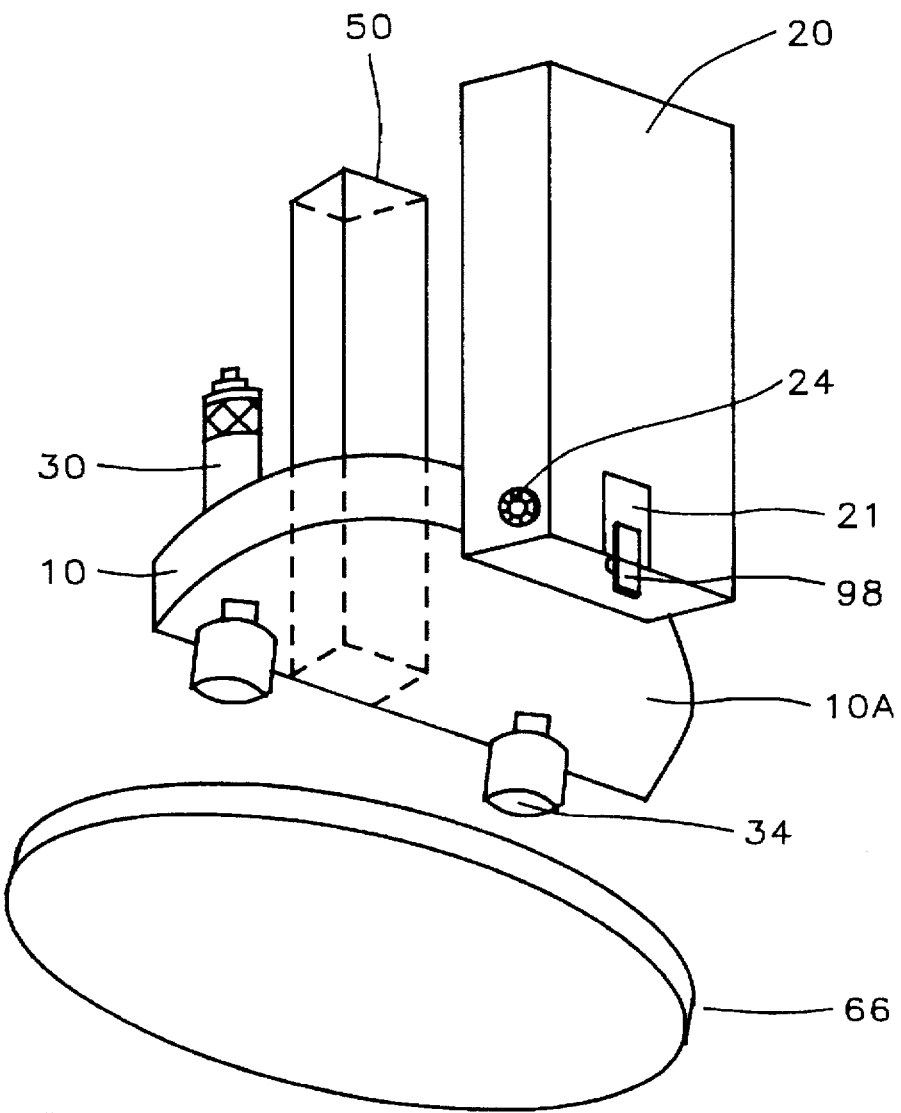
FIG. 2A

TRIPOD FOR POLISHING A SAMPLE AND FOR VIEWING THE SAMPLE UNDER A MICROSCOPE

BACKGROUND OF THE INVENTION

1) Field of the Invention

This invention relates to sample mounts for SEM, TM, and optical microscopy and particularly to a sample mount that is used for preparing samples for viewing under microscopes and more particularly to a mount for holding samples for grinding the sample and for holding the sample in focus under an optical microscope.

2) Description of the Prior Art

Scanning electron microscopes (SEM) are useful research tools which permit microscopic the evaluation of samples with much greater resolution and magnification than possible with conventional light microscopes. However, the procedure necessary to prepare and observe samples is cumbersome and requires a great deal of operator time merely to grind/polish and position the sample for the microscopic examination.

For example, to prepare samples for microscopic observation in a cross sectional view, the edge of the samples must be ground or polished to see the small structures. More particularly, when viewing a semiconductor sample, to observe the structures in cross section, an edge of the sample must be polished. The polished sample edge must be ground at a precise angle so the measurements of the elements in the sample are accurate. Often the sample is ground at a 90° angle. FIG. 1A shows a semiconductor sample 98 being observed by an objective of a scanning electron microscope (SEM), TM, or an optical microscope 60. The sample is being viewed from a top down view position. FIG. 1B shows the sample edge 99 of the semiconductor sample 98 being viewed by a microscope 60 in cross sectional view. The size of the elements in the semiconductor sample will have different measurements if the sample edge 99 is polished/ ground in different planes. FIG. 1C shows a sample edge 99 which was ground down at a 90° angle. FIG. 1D shows the same semiconductor sample edge 99 ground down at a 110° angle. The different polished angles change the measured depths 96 97 significantly. For example, if the actual depth 97 of the element is 0.35 µm, the sample element in FIG. 1D ground down at about a 110° angle, will have the incorrect measured depth 96 of 0.65 µm. Therefore, it is very important to accurately polish/grind the sample edges 99 so that accurate observations/measurements can be made.

Currently, many sample grinding operations are not performed accurately. The method of grinding samples by holding the sample 98 by hand against a polishing wheel produces inaccurate angles of the sample edges. This hand method also requires highly trained operators and consumes too much operator time.

Another shortcoming of current practices is the inability to mount the sample in a chuck that can be used to observe the sample in both the top down view (sample is a horizontal position as in FIG. 1A) and in a cross sectional view (sample in a vertical position as shown in FIG. 1B). Conventional electron microscopes are provided with a microscope stage having a planar operative upper surface within which is mounted the sample for observation. In one embodiment, the microscope stage is provided with an aperture into which a sample is placed, with the sample for observation being securely attached to the upper surface of the stage. A longitudinal axis through the center line of the aperture is disposed perpendicular to the surface of the microscope stage. Typically the electron beam from the SEM is focused about this axis which is perpendicular to the microscope stage. In order to observe the specimen in a cross section, the entire stage must be rotated 90 degrees so that the electron beam will enter the side of the specimen as opposed to the top of the sample.

Typically, an optical microscope is used to initially find and observe the desired element that is being analyzed using other tools, such as SEM and TM. Because the semiconductor structures continuously get smaller (e.g., the progression of line widths from 1.0 µm, to 0.5 µm to 0.35 µm to 0.25 µm) higher powered optical microscopes with larger lens are need to observe the samples. The higher powered microscopes have much smaller focal distances. Older microscope stages and tripods where not designed to work in these close distances and often have parts which make it difficult to get the microscope lens in close to the sample.

Another procedure often performed is turning the sample from a top down view as shown in FIG. 1A to a side view (cross sectional view) as shown in FIG. 1B. The microscope stage should allow the sample to be rotated into position and position the sample in position so that the sample is still in position. This would save the operator time in not requiring the operator to re-focus the sample. Focusing is time consuming. Therefore, a new stage is needed which positions the sample the same distance from the lens in both the top down view position and the cross-section position so the operator will not have to re-focus the sample.

While conventional procedures certainly perform adequately for their intended result, the amount of time needed to replace individual samples on a microscope stage, and the 90° degree rotation of the stage and re-focusing for cross sectional viewing of the specimen, involve an inordinate amount of time prior to making the observation with the microscope.

Therefore, there is a need for a sample preparation holder which can be used to polish semiconductor samples edges to an accurate angle. Also, there is a need to design a micrometer with a short working range without sample rotation to fit the tripod within the microscope lens working range. Also there is a need to design a tripod main body to fix the human hand for operation considerations. There is also a need for the new sample holder which can turn from a top down view to a cross section view and position the sample at the same height so that it will remain in focus. This will reduce the operator's time so that they do not have to re-focus/adjust the height of the sample. This new sample holder should be able to be used for both wafer and mask observations.

SUMMARY OF THE INVENTION

It is an objective of the present invention to provide a sample tripod holder which is used to polish/grind samples to an accurate angle, including a 90° angle.

It is also an object of the present invention to provide a sample tripod holder which will allow a sample edge to be polished to a highly accurate angle.

It is an object of the present invention to provide a sample tripod holder micrometer for a SEM and optical microscope can be used to position a sample in focus without rotating the sample.

It is another object of the present invention to provide a tripod, stage and micrometer for a SEM and optical microscope which has a low profile to allow a higher power optical microscope to be used for both the top down view and the cross-sectional view without having to adjust the sample height.

It is still another object of the present invention to provide a tripod, stage and micrometer for an SEM and optical microscope that has can be easily adjusted by the operator's hands.

To accomplish the above objectives, the present invention provides a sample holder tripod and non-rotating micrometer which positions a sample in the correct position over a grinding/polishing surface so that the sample edge is accurate. The device is called a sample holder because it holds the sample while the sample is ground and while the sample is observed by a microscope. The device is called a tripod because it rests on three supports while polishing the sample. The three supports are formed by two adjustable legs and the sample as shown in FIG. 2A. The two legs 30 and the sample 98 touch the grinding wheel 50 during the grinding of the sample. A level indicators mounted on to the tripod base 10 used to measure the angle the sample is being ground. The adjustable length legs 30 are adjusted so that the sample is ground by a grinding wheel at the desired angle.

The sample holder tripod is also used as a sample viewing stage for microscopes. The tripod is designed so that the sample position can be change between a top view and a cross sectional view and remain in focus. The tripod moves the sample from a top down view to a cross-sectional view and maintains the sample at the same distance from the microscope (e.g., still in focus) without rotating.

The sample holder tripod comprises of the present invention comprises: a tripod base, two adjustable legs, a support and a sample stage. The tripod base has a front and back side, and a top and a flat bottom. The support is mounted on the back side of the tripod base. The two adjustable legs are preferably made of linear micrometers and extend perpendicular from the back side.

The sample stage is mounted on the top of the tripod base. The sample stage has set screw with fastens the sample or sample block to the sample stage in a groove. The two adjustable legs extend through the tripod stage from the front side to the back side. The adjustable legs have knobs extending through the front side of the tripod base. It is important that the knobs do not rotate which will cause the sample to be polished unevenly. the knobs are fastened to the tripod base to prevent them from rotating.

In a preferred embodiment, the adjustable legs 30 preferably comprise linear micrometers 32. The tripod base 10 preferably includes two leg holes. The adjustable legs 30 are mounted to the tripod base 10 through the leg holes 11. The tripod base preferably further includes a bubble level indicator 40 42 mounted on the side of the tripod base 10 to measure the sample polishing angle. Also, during the sample polishing operation, the front side 10A of the tripod base 10 faces downward and a polishing tool 50 touches the tip of the sample and the end of the legs.

The sample tripod holder has many advantages over the prior art. The sample holder tripod of the current invention is used to position the sample at an accurate angle from a polishing surface so that the sample edge has a planar surface. The tripod of the current invention has a smaller size that allows a larger, higher objective lens to be used to see the specimen. This allows a conventional microscope to be used as opposed to an expensive inverse type optical microscope. Moreover, the tripod of the invention has a leveling bubble to monitor and measure the sample grinding angle. The tripod keeps the sample in focus when the tripod turns from the top down view position to the cross-section view position thereby shortening the operator time to focus the sample.

BRIEF DESCRIPTION OF THE DRAWINGS

The features and advantages of the sample holder tripod, stage and adjustable micrometer legs according to the present invention and further details such device in accordance with the present invention will be more clearly understood from the following description taken in conjunction with the accompanying drawings in which like reference numerals designate similar or corresponding elements, regions and portions and in which:

FIG. 1A is a three dimensional view of a semiconductor sample in a top plan view position being viewed by a microscope in a top down view.

FIG. 1B is a three dimensional view of a semiconductor sample being viewed by a microscope in a cross sectional view position.

FIG. 1C is a perspective view of a sample having a 90° ground edge.

FIG. 1D is perspective view of a sample illustrating about a 110° ground edge.

FIG. 2A is a three dimensional view of the sample holder tripod of the current invention holding a sample in a proper position (e.g., 90°) over a grinding wheel.

DETAILED DESCRIPTION OF THE PREFERRED EMBODIMENTS

Figure 2B:
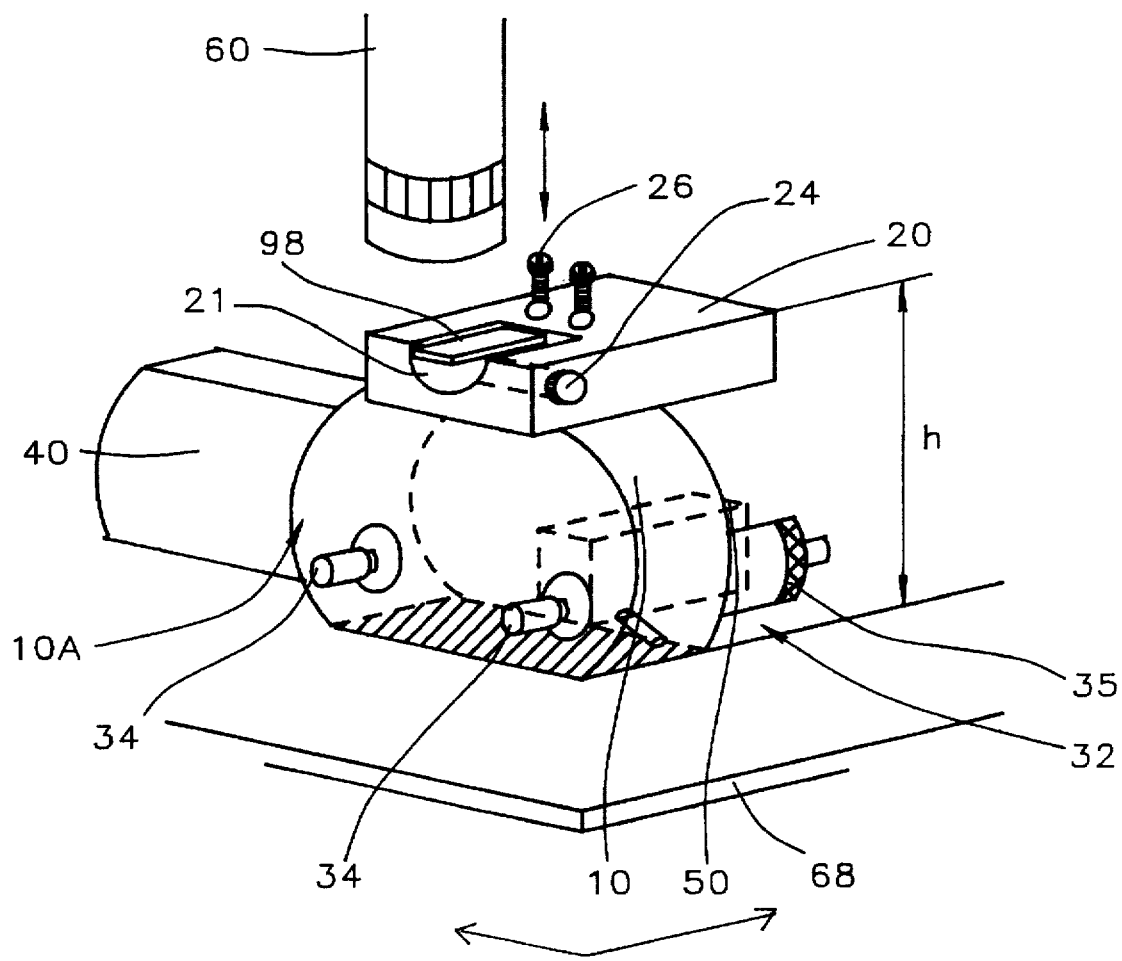
FIG. 2B is a three dimensional view the sample holder tripod of the current invention showing the orientation of the tripod and microscope lens in the top down view position.

The present invention will be described in detail with reference to the accompanying drawings. The present invention provides a sample holder tripod and non-rotating micrometer for polishing precise angles of sample edges. The device is called a tripod because it rests on three supports while polishing the sample. As shown in FIG. 2A, the three supports are two adjustable legs 30 and the sample 98 (sample stage 20). The two legs 30 and the sample 98 touch the grinding wheel 66 during the grinding of the sample 98. A level indicator 40 (see FIG. 4A) mounted on to the tripod base 10 is used to measure the angle the sample is being ground. The adjustable length legs 30 are adjusted so that the sample is ground at the desired angle.

Figure 3:
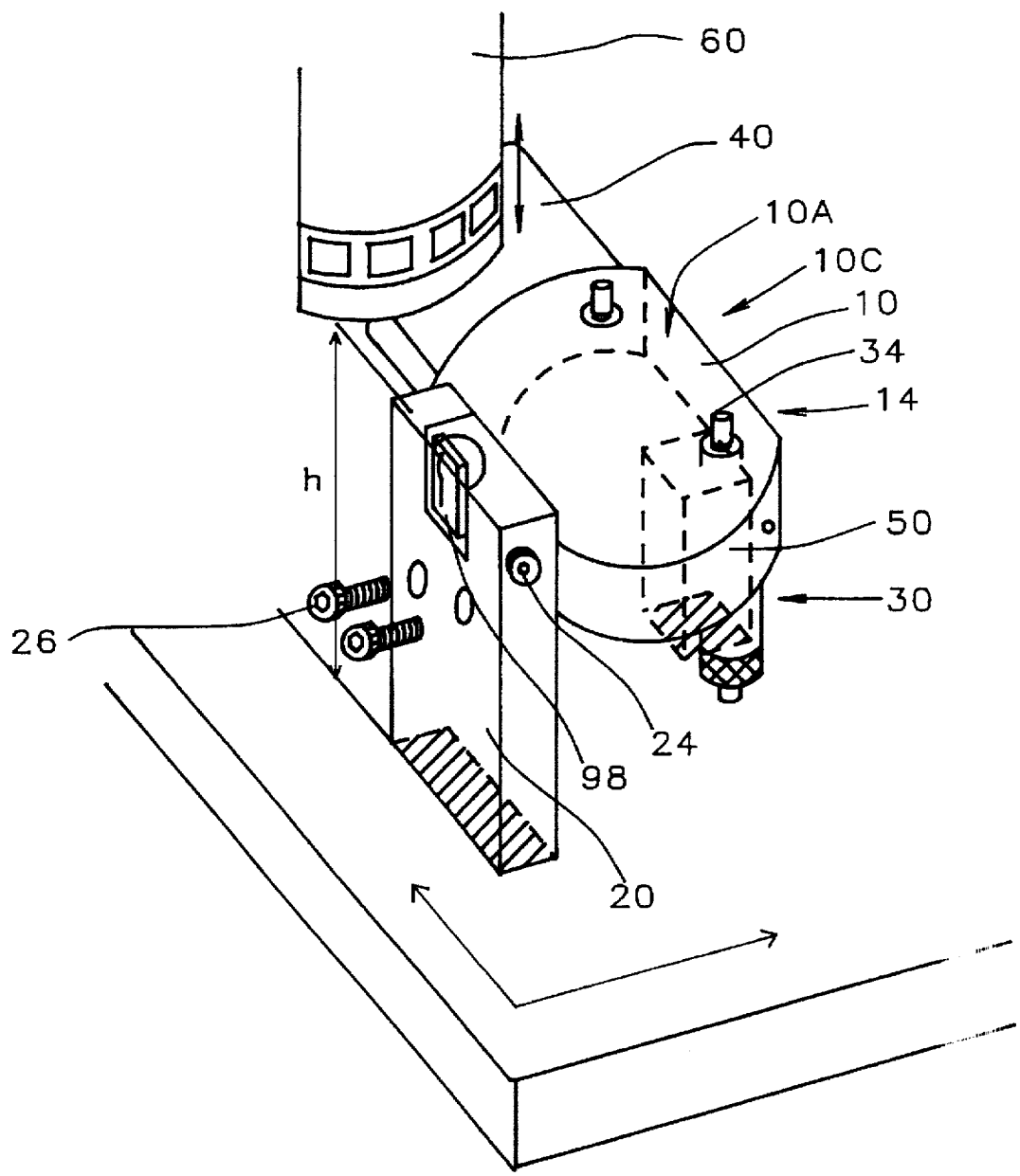
FIG. 3 is a three dimensional view the sample holder tripod of the current invention showing the orientation of the tripod and microscope lens in the cross sectional view position.

The sample holder tripod is also used as a viewing stage for microscopes as shown in FIGS. 2B and 3. The tripod is designed so that the sample position can be rotated between a top view and a cross sectional view and remain in focus. The tripod dimension are designed so that the heights (h) of the sample 98 is the same for both the top down views position (FIG. 2b) and the cross-sectional view position 3 (FIG. 3). The tripod 14 can move the sample 98 from a top down view to a cross-sectional view and maintain the sample at the same distance from the microscope 60 (e.g., still in focus).

As shown in FIGS. 2A, 2B, 3, 4A, 4B and 4C the sample holder tripod preferably comprises: a tripod base 10, two adjustable legs 30, a support 50, a sample stage 20 and a level monitor assemble 40 42. The tripod base 10 has a front 10A and back side 10B and a top and a flat bottom 10C. When the tripod is used to polish a sample, the front side 10A faces the polishing tool 50 as shown in FIG. 2A. The major elements of the tripod sample are listed below in table 1.

TABLE 1

| Elements of the Tripod sample holder | |
|---|---|
| tripod base | 10 |
| front side of tripod base | 10A |
| back of tripod base | 10B |
| flat bottom of tripod base | 10C |
| leg holes in tripod base | 11 |
| sample stage mounting holes | 12 |
| overall sample holder tripod | 14 |
| sample stage | 20 |
| center groove in sample stage | 21 |
| set screws for sample stage | 24 |
| sample stage fix screws | 26 |
| Two adjustable legs | 30 |
| micrometer assembly | 32 |
| Bottom of legs | 34 |
| Lever indicator | 40 |
| Bubble level indicator | 42 |
| support | 50 |
| SEM or other microscope | 60 |
| polishing tool surface | 66 |
| microscope stage | 68 |
| sample | 98 |
| sample edge/end | 99 |

Figure 5:
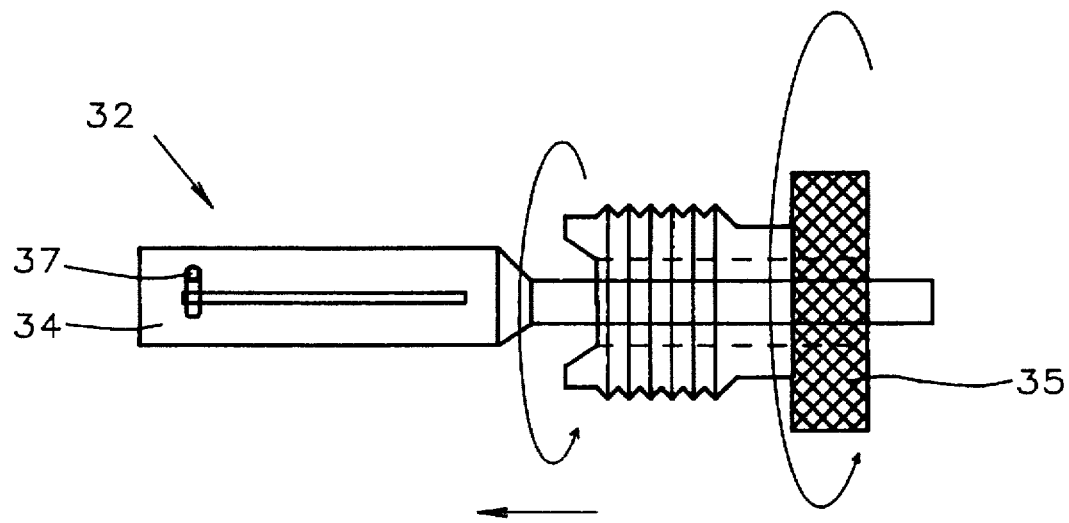
FIG. 5 is a preferred embodiment of the present invention wherein the adjustable legs of the sample holder tripod comprise a linear micrometer assembly.

As shown in FIGS. 2A, and 5 the adjustable legs 30 preferably comprise micrometer assemblies 32 that are used to adjust the distance the two adjustable legs 30 extend from the front side 10A of the sample base 10. The micrometers allow the two adjustable legs 30 and the sample tip 98 to be adjusted to be in one plane so that a polishing tool 50 can polish the sample tip 99 yielding a flat planar polished sample tip.

In a preferred embodiment, the adjustable legs 30 comprise linear micrometers 32. As shown in FIG. 5, the micrometer assembly 32 preferably comprises a knob 34, a pin 37 and an adjustment head 35. It is important that the knob 34 does not rotate, especially during the grinding operation. The knob 34 is held in position by pin 37. The length of the micrometer is adjusted by rotating the adjustment head 35. The micrometer assemble 32 preferably has a working range of between about 4 to 8 mm and more preferably about 6 mm linear motion without knob 34 rotation.

The ends 34 (knobs) of the legs 30 in contact with the grinding wheel 50 are preferably made of PVDF or PVC (Polyvinyl chloride) material. See FIG. 2. Also, the bubble level indicator 42 is used by the operator to keep the sample grinding at the proper angle.

Figure 4A:
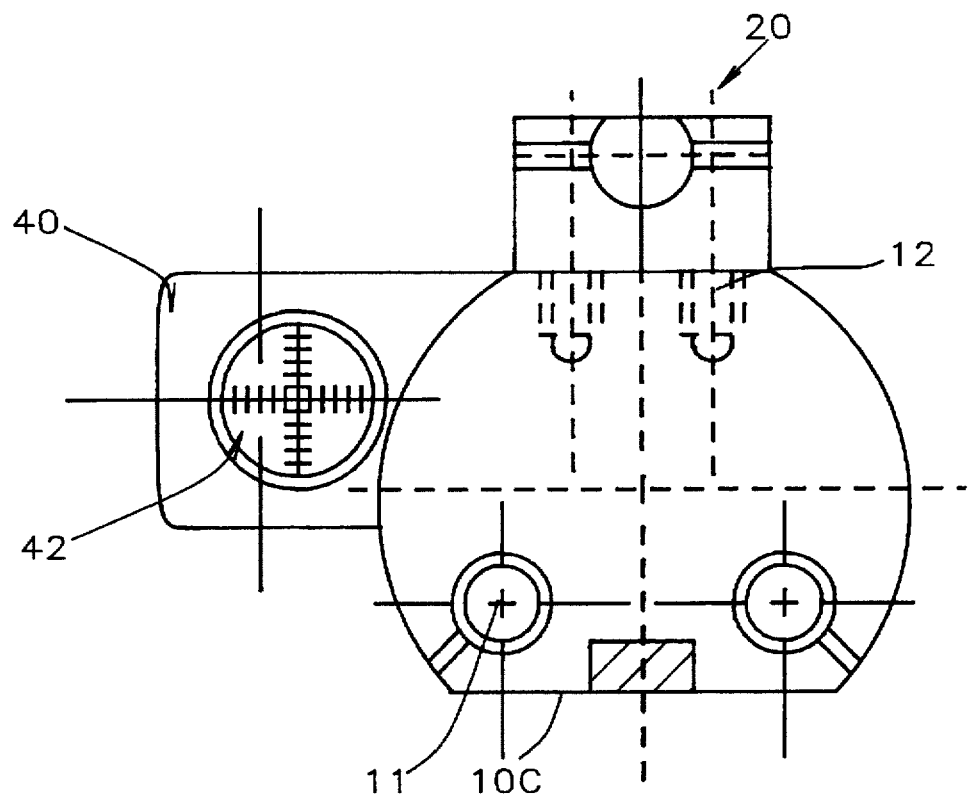
FIG. 4A is a side view of the sample holder tripod of the current invention.
Figure 4B:
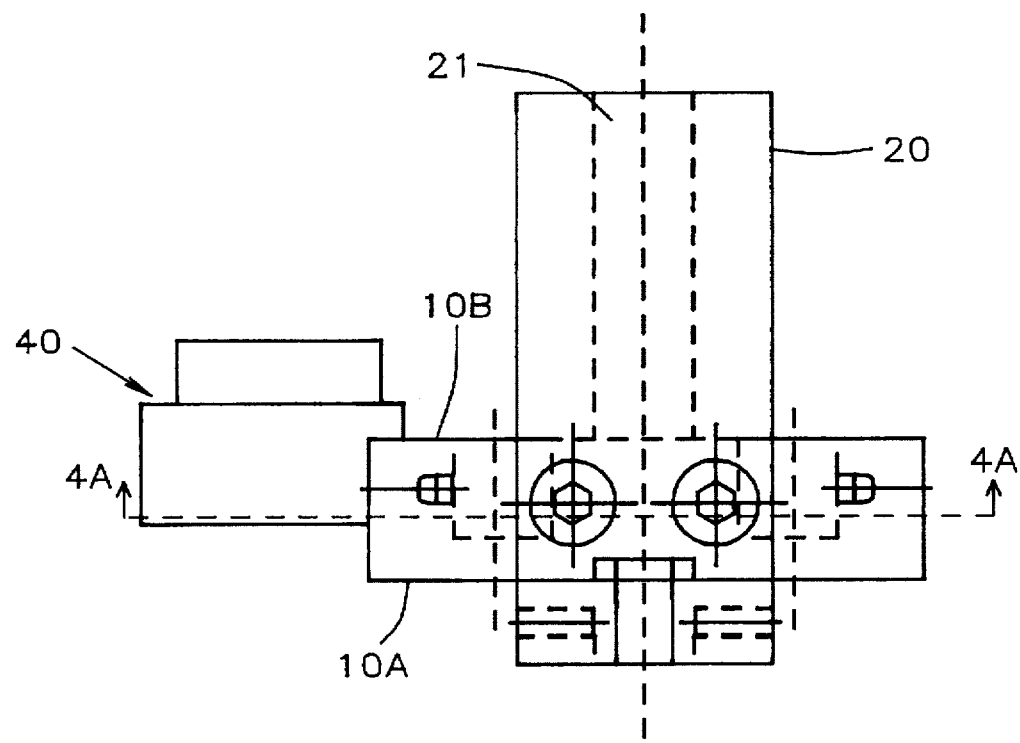
FIG. 4B is a top down view of the sample holder tripod of the current invention.
Figure 4C:
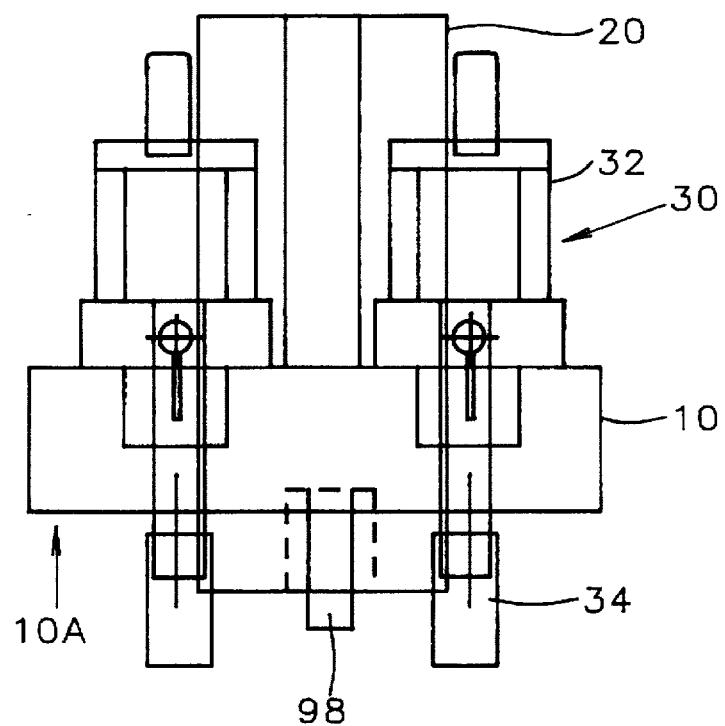
FIG. 4C is a bottom up view of the sample holder tripod of the current invention.

As shown in FIG. 4A, the tripod base 10 preferably includes two leg holes 11. The adjustable legs 30 are mounted to the tripod base 10 through the leg holes 11. The base 10 is preferably formed of aluminum, stainless steel or bronze, and more preferably formed of aluminum.

Referring to FIG. 4a, the sample holder tripod base 10 preferably further includes a level indicator 40. The level indicator shows the angle that the polishing tool is grinding the sample. The level indictor is preferably a bubble level indicator 42.

As shown in FIGS. 2A, 2B and 3, the sample stage 20 holds a sample 98. The sample 98 is often held in a sample block. The sample 98 has a sample tip 99 facing away from the front side 10A of the tripod base 10. The two adjustable legs 30 and the sample stage 20 mounted on the front side 10A of the tripod base 10. The stage 20 has a central groove 21 where said sample 98 is positioned. The stage 20 is preferably formed of aluminum.

As shown in FIG. 4, leg holes pass in a z-direction through the tripod base 10. The stage mounting holes 12 pass in a y-direction through the tripod base 10.

As shown in FIG. 2A, the sample holder tripod 14 is used to polish a sample 98. The front side 10A of the tripod base 10 faces downward. The invention further includes a polishing tool 66 touching the tip 99 of the sample 98 and the end of the legs 30. The bottom section (knob) 34 of the legs 30 is made of PVDF or acrylic material that resists grinding by the grinding tool 66.

As shown in FIG. 2B, when the tripod is used to hold the sample during a top down view microscopic observation, the front side 10A of the tripod base 10 is facing horizontally. A microscope 60 is positioned vertically above the sample tip and the microscope is focused on the sample tip 99.

The sample polished and focused can be any type of sample, (e.g. biological) and is preferably a semiconductor related sample, such as a semiconductor substrate or a mask.

The sample holder tripod has numerous advantages over the prior art. First, the sample holder tripod of the current invention is used to position the sample at an accurate angle (e.g., 90°) from a polishing surface so that the sample edge has a planar (e.g., 90°) surface. Also, the micrometer 30 of the of the current invention is designed so that the bottom knob 34 does not rotate thus maintaining the proper grinding angle during sample grinding operations.

Third, the tripod of the current invention has a smaller size that allows a larger, higher objective lens to be used to see the specimen. This allows a conventional microscope to be used as opposed to an expensive inverse type optical microscope.

Fourth, the tripod has a leveling bubble to monitor operation trend. The tripod keeps the sample in focus when the tripod turns from the top down view to the cross-sectional view thereby shortening the operator time to focus the sample. This saves valuable operator time.

While the invention has been particularly shown and described with reference to the preferred embodiments thereof, it will be understood by those skilled in the art that various changes in form and details may be made without departing from the spirit and scope of the invention.

What is claimed is:

1. A sample holder tripod for polishing a sample and viewing a sample with a microscope, comprising:

a) a tripod base, two adjustable legs, a support and a sample stage;

b) said tripod base having a front and back side, and a top and a flat bottom;

c) said support mounted on said back side of said tripod base; said two adjustable legs extending perpendicular from said back side;

d) said sample stage mounted on said top of said tripod base; said sample stage having a means of mounting a sample;

e) said two adjustable legs extending through the tripod stage from said front side to said back side; said adjustable legs having knobs extending through said front side of said tripod base.

2. The sample holder tripod of claim 1 wherein said adjustable legs comprise linear micrometers.

3. The sample holder tripod of claim 1 wherein said tripod base includes two leg holes; said adjustable legs are mounted to said tripod base through said leg holes; and said adjustable legs comprise linear micrometers.

4. The sample holder tripod of claim 1 wherein said tripod base is formed of aluminum material.

5. The sample holder tripod of claim 1 wherein said sample stage has a central groove where said sample is positioned; said sample stage has a set screw for holding said sample.

6. The sample holder tripod of claim 1 wherein said tripod base further includes a level indicator.

7. The sample holder tripod of claim 1 wherein said tripod base further includes a bubble assemble having a bubble lever indicator mounted on the side of said tripod base.

8. The sample holder tripod of claim 1 wherein said means to mount a sample comprises a sample set screw; and said sample set screw holds said sample in said sample stage.

9. The sample holder tripod of claim 1 wherein said front side of said tripod base is facing downward and which further includes a polishing tool touching the tip of said sample and said knobs of said adjustable legs.

10. The sample holder tripod of claim 1 wherein said front side of said tripod base is facing horizontally and which further includes a scanning electron microscope (SEM) positioned vertically above said sample tip; said scanning electron microscope focused on said sample tip.

11. The sample holder tripod of claim 1 wherein said the height (h) of the tripod base to the top of said sample holder is less than the working focal length of a microscope observing said sample.

12. A sample holder tripod for polishing a sample and viewing a sample with an optical microscope, comprising:
   a) a tripod base, two adjustable legs, a support and a sample stage;
   b) said tripod base having a side, front and back side, and a top and a flat bottom; said tripod base having a level indicator assembly mounted on said side of said tripod base;
   c) said support mounted on said back side of said tripod base; said support extending perpendicular from said back side;
   d) said sample stage mounted on said top of said tripod base; said sample stage having a set screw for mounting a sample in said sample stage;
   e) said two adjustable legs extending through the tripod stage from said front side to said back side; said two adjustable legs comprising linear micrometers; said micrometers having knobs which are fastened to said tripod base and an adjustment head; said knobs extending through said front side of said tripod base, whereby said two adjustable legs and said sample tip can be adjusted to be in one plane so that a polishing tool can polish said sample tip yielding a flat planar polished sample tip.

13. The sample holder tripod of claim 12 wherein said tripod base includes two leg holes; said adjustable legs are mounted to said tripod base through said leg holes.

14. The sample holder tripod of claim 12 wherein said tripod base is formed of aluminum material.

15. The sample holder tripod of claim 12 wherein said sample stage has a central groove where said sample is positioned.

16. The sample holder tripod of claim 12 wherein said level indicator assembly having a bubble lever indicator.

17. The sample holder tripod of claim 12 wherein said front side of said tripod base is facing downward and which further includes a polishing tool touching the tip of said sample and said knobs of said adjustable leg extensions.

18. The sample holder tripod of claim 12 wherein said front side of said tripod base is facing horizontally and which further includes a scanning electron microscope (SEM) positioned vertically above said sample tip; said scanning electron microscope focused on said sample tip.

* * * * *